(12) United States Patent
Maubru

(10) Patent No.: US 6,180,118 B1
(45) Date of Patent: *Jan. 30, 2001

(54) COMPOSITION AND ITS USES FOR THE DYEING, PERMANENT RESHAPING OR BLEACHING OF THE HAIR

(75) Inventor: Mireille Maubru, Chatou (FR)

(73) Assignee: L'Oréal, Paris (FR)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/931,561

(22) Filed: Sep. 16, 1997

(30) Foreign Application Priority Data

Sep. 17, 1996 (FR) .................................................. 96 11318

(51) Int. Cl.$^7$ ............................... A61K 6/00; A61K 7/00; A61K 7/06; A61K 7/135
(52) U.S. Cl. ........................... 424/401; 424/62; 424/70.11
(58) Field of Search .................. 424/78.03, 70.11, 424/70.15, 70.17, 401, 62

(56) References Cited

U.S. PATENT DOCUMENTS

| | | |
|---|---|---|
| 3,499,844 | 3/1970 | Kibbel et al. . |
| 4,128,631 | 12/1978 | Lundmark et al. ................ 424/70 |
| 4,685,931 | 8/1987 | Schieferstein et al. .................. 8/406 |
| 4,781,923 | 11/1988 | Pellico ................................ 424/130 |
| 4,804,705 | 2/1989 | Pum et al. ......................... 525/54.21 |
| 4,927,627 | 5/1990 | Schrader et al. ...................... 424/62 |
| 5,368,850 | 11/1994 | Cauwet et al. ........................ 424/70 |
| 5,470,551 | * 11/1995 | Dubief ............................. 424/70.12 |
| 5,531,993 | 7/1996 | Griat ................................... 424/401 |
| 5,587,145 | 12/1996 | Lion et al. ............................ 424/45 |
| 5,660,820 | * 8/1997 | Mondet ............................ 424/70.16 |
| 5,684,104 | * 11/1997 | Funk ................................ 526/232.2 |
| 5,688,514 | * 11/1997 | Chaudbury et al. ................. 424/401 |

FOREIGN PATENT DOCUMENTS

| | | |
|---|---|---|
| 0 184 785 | 6/1986 | (EP) . |
| 0 308 825 | 3/1989 | (EP) . |
| 0060 4249 A1 | * 6/1994 | (EP) . |
| 0 611 566 | 8/1994 | (EP) . |
| 0642781 | 3/1995 | (EP) . |
| 23 80774 | 9/1978 | (FR) . |
| 26 98004 | 5/1994 | (FR) . |
| 27 10263 | 3/1995 | (FR) . |
| 27 18640 | 10/1995 | (FR) . |

OTHER PUBLICATIONS

Chemical Abstracts, vol. 96, No. 18, May 3, 1982, p. 405.
English Derwent Abtract of FR 2 710 263., Sep. 21, 1993.

* cited by examiner

Primary Examiner—Thurman K. Page
Assistant Examiner—S. Howard
(74) Attorney, Agent, or Firm—Finnegan, Henderson, Farabow, Garrett & Dunner, L.L.P.

(57) ABSTRACT

A cosmetic composition intended for treating a keratin substance, comprising, preferably in a support suitable for keratin substances:

(a) at least one crosslinked and at least 90% neutralized poly(2-acrylamido-2-methylpropanesulphonic acid) polymer and (b) at least one oxidizing agent selected from hydrogen peroxide and compounds capable of producing hydrogen peroxide by hydrolysis, such as persalts and urea peroxide.

37 Claims, No Drawings

COMPOSITION AND ITS USES FOR THE DYEING, PERMANENT RESHAPING OR BLEACHING OF THE HAIR

The present invention relates to a composition, preferably a gelled oxidizing composition, intended for treating a keratin substance comprising at least one polymer selected from crosslinked and at least 90% neutralized poly(2-acrylamido-2-methylpropanesulphonic acid) polymers, as well as to its uses for the dyeing, permanent reshaping or bleaching of the hair.

It is known to dye keratin fibres, and in particular human hair, with dye compositions containing oxidation dye precursors, in particular ortho- or para-phenylene diamines, orth- or para-aminophenols, and heterocyclic compounds, these generally being referred to as oxidation bases. Oxidation dye precursors, or oxidation bases, are colourless or weakly coloured compounds which, when combined with oxidizing products, can give rise to coloured compounds and dyes by a process of oxidative condensation. It is also known that the shades obtained with these oxidation bases can be varied by combining them with couplers or colour modifiers, the latter being chosen in particular from aromatic meta-diamines, meta-aminophenols, meta-diphenols and certain heterocyclic compounds such as indole compounds.

The oxidizing agent present in the composition as defined above can be chosen from the oxidizing agents used conventionally for the oxidation dyeing of keratin fibres, and among which mention may be made of hydrogen peroxide or compounds capable of producing hydrogen peroxide by hydrolysis such as urea peroxide, and persalts such as perborates and persulphates. Hydrogen peroxide is particularly preferred.

It is known that the most common technique for permanently reshaping the hair comprises the steps of, in a first stage, opening the -S-S-disulphide bonds of keratin (cystine) using a composition containing a suitable reducing agent (the reduction step), followed, after the hair thus treated has been rinsed, by re-forming, in a second stage, the said disulphide bonds by applying to the hair, which has been placed under tension (curlers and the like) beforehand, an oxidizing composition (the oxidation step, also known as the fixing step) in order, finally, to give the hair the desired shape. This technique thus makes it possible either to make the hair wavy or to straighten it or remove curls therefrom. The new shape given to the hair by a chemical treatment as above is remarkably long-lasting and withstands the action of washing with water or shampoo, this being in contrast with simple standard techniques of temporary reshaping such as hairsetting.

The reducing compositions which may be used to carry out the first step of a permanent-wave operation generally contain sulphites, bisulphites, alkylphosphines or, preferably, thiols as reducing agents. Among these agents, those commonly used are cysteine and its various derivatives, cysteamine and its derivatives, thiolactic acid or thioglycolic acid, salts thereof and esters thereof, in particular glyceryl thioglycolate.

In regards to the oxidizing compositions required to carry out the fixing step, compositions based on aqueous hydrogen peroxide solution are usually used in practice.

Attempts to develop cosmetic formulations in the form of transparent gels have been continuing for many years. This type of presentation is particularly favoured by consumers for aesthetic reasons and for reasons of ease and comfort of use.

The gel form usually corresponds to a practical concern of the formulator, namely, to facilitate the removal of the product from its container without any significant loss, limit the spread of the product to the local area of treatment and enable it to be used in sufficient amounts to obtain the desired cosmetic effect. These aims are important for the oxidizing formulations used in hair dyeing, for permanent-waving or for bleaching of the hair. It is desired that the formulations spread well and distribute themselves uniformly along the keratin fibres and not run down the forehead, the nape of the neck, the face or into the eyes.

It is generally difficult to produce gels based on peroxide, such as hydrogen peroxide, which are stable on storage by using standard water-soluble gelling agents and/or thickeners, for example those of the crosslinked acrylic polymer type such as those sold under the name Carbopol by the company Goodrich. Peroxides are used in cosmetics in the form of acidic aqueous solutions for reasons of stability. In the presence of standard gelling agents, they usually cause appreciable variations in the viscosity of the gel during storage.

Gels are known from U.S. Pat. No. 4,804,705, the disclosure of which is specifically incorporated by reference herein, which are based on hydrogen peroxide containing a gelling agent formed by reaction of a quaternized hydroxyethyl cellulose such as Celquat (product sold by National Starch), a 15% by weight aqueous solution of a non-crosslinked poly(2-acrylamido-2-methylpropanesulphonic acid) polymer such as Cosmedia HSP-1180 (product sold by Henkel) and a poly(sodium styrenesulphonate) such as Flexan 3 (product sold by National Starch), which are used in specific concentrations.

The inventor has discovered, surprisingly, a novel family of thickeners and/or gelling agents which makes it possible to obtain transparent gels based on hydrogen peroxide or on oxidizing compound capable of releasing hydrogen peroxide, these gels being stable on storage. They are crosslinked and at least 90% neutralized poly(2-acrylamido-2-methylpropanesulphonic acid) polymers. These novel gelling agents do not affect the oxidizing properties of the hydrogen peroxide, or of a compound capable of producing hydrogen peroxide by hydrolysis, present in the gel thus formed.

The subject of the present invention is thus a cosmetic and/or dermatological composition intended for treating a keratin substance, comprising, preferably in a support which is suitable for a keratin substance:

(a) at least one polymer selected from crosslinked and at least 90% neutralized poly(2-acrylamido-2-methylpropanesulphonic acid) polymers, and (b) at least one oxidizing agent selected from hydrogen peroxide and compounds capable of producing hydrogen peroxide by hydrolysis.

The invention also relates to the use of these polymers as thickeners and/or gelling agents in cosmetic and/or dermatological compositions comprising at least one oxidizing agent selected from hydrogen peroxide and compounds capable of producing hydrogen peroxide by hydrolysis.

The crosslinked and completely or almost completely neutralized poly(2-acrylamido-2-methylpropanesulphonic acid) polymers in accordance with the invention are generally characterized in that they comprise, distributed randomly:

a) from 90 to 99.99%, preferably 99.9%, by weight of units of formula (1):

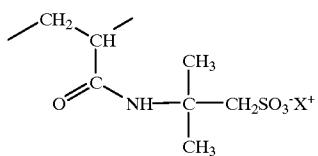

in which $X^+$ denotes a cation or a mixture of cations, not more than 10 mol % of which cations $X^+$ may be protons $H^+$;

b) from 0.01 to 10% by weight of crosslinking units derived from at least one monomer having at least two olefinic double bonds; the weight proportions being defined relative to the total weight of the polymer.

Preferably, the polymers of the invention contain a number of units of formula (1) in a sufficiently large amount to obtain polymer particles whose hydrodynamic volume in aqueous solution has a radius ranging from 10 to 500 nm and whose distribution is homogeneous and unimodal.

The polymers according to the invention which are more particularly preferred comprise from 98 to 99.8%, preferably 99.5%, by weight of units of formula (1) and from 0.2 to 2% by weight of crosslinking units.

$X^+$ represents a cation or a mixture of cations chosen in particular from a proton, an alkali metal cation, a cation equivalent of an alkaline-earth metal or the ammonium ion.

More particularly, 90 to 100 mol % of the cations are $NH_4^+$ cations and 0 to 10 mol % are protons ($H^+$).

Crosslinking monomers having at least two olefinic double bonds are chosen, for example, from dipropylene glycol diallyl ether, polyglycol diallyl ethers, triethylene glycol divinyl ether, hydroquinone diallyl ether, tetrallyloxethanoyl or other polyfunctional allyl or vinyl ether alcohols, tetraethylene glycol diacrylate, triallylamine, trimethylolpropane diallyl ether, methylenebisacrylamide and divinylbenzene.

Crosslinking monomers having at least two olefinic double bonds are more particularly chosen from those corresponding to formula (2) below:

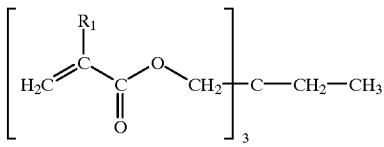

in which $R_1$ denotes a hydrogen atom or a $C_1$–$C_4$ alkyl and more particularly methyl (trimethylolpropane triacrylate).

The reaction for the polymerization of the polymers of the invention produces not only linear chains but also branched or crosslinked polymer molecules. These molecules may be characterized in particular by their rheological behaviour in water, but more particularly by dynamic light scattering.

In the case of characterization of the molecules by dynamic light scattering, the distribution of the hydrodynamic volume of the polymer structures is measured. The macromolecules dissolved in water are flexible and surrounded by a solvation sheath formed of water molecules. With charged polymers such as those of the invention, the size of the molecules depends on the amount of salt in the water. In polar solvents, the uniform charge along the main chain of the polymer leads to a considerable expansion of the polymer chain. Increasing the amount of salt increases the amount of electrolyte in the solvent and separates the uniform charges of the polymer. In addition to the molecules transported in the solvation sheath, the solvent molecules are bound in the polymer cavities. In this case, the solvent molecules form part of the macromolecules in solution and move at the same average speed. Thus, the hydrodynamic volume describes the linear size of the macromolecule and of these solvation molecules.

The hydrodynamic molecule $v_h$ is determined by the following formula:

$$v_h = M/N_A \times (V_2 + dV_1)$$

where:

M denotes the mass in grams of the non-dissolved macromolecule;

$N_A$ denotes the Avogadro number;

$V_1$ denotes the specific volume of the solvent;

$V_2$ denotes the specific volume of the macromolecule;

d is the mass in grams of the solvent which is associated with 1 gram of non-dissolved macromolecule.

If the hydrodynamic particle is spherical, it is easy to calculate the hydrodynamic radius from the hydrodynamic volume, by the formula:

$$v_h = 4\pi R^3/3$$

where R denotes the dynamic radius.

The cases in which the hydrodynamic particles are perfect spheres are extremely rare. Most synthetic polymers involve compact structures or ellipsoids of high eccentricity. In this case, the radius is determined on a sphere which is equivalent from a friction point of view to the shape of the particle considered.

As a general rule, the calculations are done on molecular weight distributions and thus on hydrodynamic volume and radius distributions. For polydispersed systems, the distribution of the diffusion coefficients should be calculated. From this distribution, the results relating to the radial distribution and the hydrodynamic volume distribution are deduced.

The hydrodynamic volumes of the polymers of the invention are determined in particular by dynamic light scattering from the diffusion coefficients D according to the Stokes-Einstein formula: $D = kT/6\pi\eta R$ where k is the Boltzmann constant, T the absolute temperature in degrees Kelvin, $\eta$ is the viscosity of the solvent (water) and R is the hydrodynamic radius.

These diffusion coefficients D are measured by the method of characterizing a polymer mixture by laser scattering, described in the following references:

(1) Pecora, R; Dynamic Light Scattering; Plenum Press, New York, 1976;

(2) Chu, B; Dynamic Light Scattering; Academic Press, New York, 1994;

(3) Schmitz, KS; Introduction to Dynamic Light Scattering; Academic Press, New York, 1990;

(4) Provincher S. W.; Comp. Phys., 27, 213, 1982;

(5) Provincher S. W.; Comp. Phys., 27, 229, 1982;

(6) ALV Laservertriebgesellschaft mbH, Robert Bosch Str. 47, D-63225 Langen, Germany;

(7) ELS-Reinheimer Strasse 11, D-64846 Gross-Zimmem, Germany;

(8) CHI WU et al, Macromolecules, 1995, 28, 4914–4919, the disclosures of which are specifically incorporated by reference herein.

The polymers particularly preferred are those having a viscosity of greater than or equal to 1000 cps and more preferably ranging from 5000 to 40,000 cps and more particularly from 6500 to 35,000 cps, preferably measured with a Brookfield viscometer, rotor 4, at a spin speed of 100 revolutions/minute in aqueous 2% solution and at 25° C.

The crosslinked poly(2-acrylamido-2-methylpropanesulphonic acid) polymers of the invention may be obtained by the preparation process comprising the following steps:

(a) the 2-acrylamido-2-methylpropanesulphonic acid monomer is dispersed or dissolved in free form in a solution of tert-butanol or water and tert-butanol;

(b) the monomer solution or dispersion obtained in (a) is neutralized with one or more inorganic or organic bases, preferably aqueous ammonia $NH_3$, in an amount that will give a degree of neutralization of the sulphonic acid functions of the polymer ranging from 90 to 100%;

(c) the crosslinking monomer(s) is (are) added to the solution or dispersion obtained in (b);

(d) a standard radical polymerization is carried out in the presence of free-radical initiators at a temperature ranging from 10 to 150° C., the polymer precipitating out in the tert-butanol-based dispersion or solution.

The crosslinked, completely or almost completely neutralized poly(2-acrylamido-2-methylpropanesulphonic acid) polymers are present in the cosmetic or dermatological compositions of the invention in concentrations preferably ranging from 0.01 to 10% by weight relative to the total weight of the composition and more preferably from 0.05 to 5% by weight.

The oxidizing agent of the composition according to the invention is preferably chosen from the group formed by aqueous hydrogen peroxide solution, urea peroxide and persalts such as perborates or persulphates, or mixtures thereof.

Preferably, the oxidizing agent is hydrogen peroxide.

The hydrogen peroxide concentration may range preferably from 0.5 to 40 volumes, more preferably from 2 to 30 volumes, and the concentration of compound capable of forming hydrogen peroxide by hydrolysis may range from 0.1 to 25% by weight relative to the total weight of the oxidizing composition.

The compositions, preferably oxidizing compositions, according to the invention may be anhydrous or aqueous.

The compositions, preferably oxidizing compositions, according to the invention are preferably aqueous, and the pH of the entire aqueous composition preferably ranges from 1 to 13 and even more preferably from 2 to 12.

The composition, preferably oxidizing composition, may also be, particularly in the case of bleaching, in the form of two parts to be mixed together at the time of use, one of these two parts containing alkaline agents and being in solid or liquid form. For hydrogen peroxide, the pH is preferably below 7 before mixing.

The pH of the aqueous compositions, preferably oxidizing compositions, according to the invention may be obtained and/or adjusted conventionally by adding either basifying agents, such as, for example, aqueous ammonia, monoethanolamine, diethanolamine, triethanolamine, isopropanolamine, 1,3-propanediamine, an ammonium or alkali metal carbonate or bicarbonate, an organic carbonate such as guanidine carbonate, or an alkaline hydroxide, it being possible, of course, for all of these compounds to be taken alone or mixed, or by adding acidifying agents such as, for example, hydrochloric acid, acetic acid, lactic acid or boric acid.

The compositions, preferably oxidizing compositions, may contain additives known for their use in oxidizing compositions for the oxidation dyeing of the hair or for the permanent reshaping or bleaching of the hair, such as basifying or acidifying agents, preserving agents, sequestering agents, opacifiers and optionally a conditioner. It may be in the form of a shampoo.

The compositions according to the invention are generally in the form of a transparent gel. Their viscosity preferably ranges from 50 centipoises to 100 poises and more preferably from 75 centipoises to 5 poises.

Another subject of the invention is a process for the oxidation dyeing of keratin fibres, and in particular human keratin fibres such as the hair, using a dye composition comprising, in a support which is suitable for dying keratin fibres, at least one oxidation dye precursor and at least one oxidizing composition, as defined above.

According to this process, at least one dye composition as defined above is applied to the fibres, the colour being developed at acidic, neutral or basic pH using an oxidizing composition, according to the invention which is applied simultaneously or sequentially, with or without intermediate rinsing.

According to a particularly preferred embodiment of the dyeing process according to the invention, the dye composition described above is mixed, at the time of use, with an oxidizing composition according to the invention. The mixture obtained is then applied to the keratin fibres and is left in place for preferably 3 to 50 minutes approximately, more preferably 5 to 30 minutes approximately, after which the fibres are rinsed, washed with shampoo, rinsed again and dried.

Another subject of the present invention is a process for the permanent reshaping of keratin fibres, and in particular the hair, using the composition defined above as the oxidizing composition.

The first step in this process is the application of a reducing composition to the hair. This application is carried out lock by lock or all at once.

The reducing composition comprises at least one reducing agent, which may in particular be chosen from thioglycolic acid, cysteine, cysteamine, glyceryl thioglycolate, thiolactic acid, or salts of thiolactic or thioglycolic acid.

The usual step of placing the hair under tension in a shape corresponding to the desired final shape for this hair (for example curls) may be carried out by any suitable means, in particular mechanical means, known per se in order to keep the hair under tension, such as, for example, rollers, curlers or the like.

The hair may also be placed in shape without the aid of external means, simply with the fingers.

Before proceeding to the following optional rinsing step, the hair on which the reducing composition has been applied should, as is conventional, be left to stand for a few minutes, generally from 5 minutes to one hour, preferably from 10 to 30 minutes, in order to give the reducing agent plenty of time to act properly on the hair. This wait preferably takes place at a temperature ranging from 35° C. to 45° C., preferably while also protecting the hair with a bonnet.

In the second, optional, step of the process (step (ii)), the hair impregnated with the reducing composition is then rinsed carefully with an aqueous composition.

Next, in a third step (step (iii)), the oxidizing composition of the invention is applied to the rinsed hair in order to fix the hair in the new imposed shape.

As when applying the reducing composition, the hair on which the oxidizing composition has been applied is then, as is conventional, generally left for a period of a few minutes, preferably from 3 to 30 minutes, and more preferably from 5 to 15 minutes.

The vehicle for the reducing and oxidizing compositions used according to the invention is preferably water or an aqueous-alcoholic solution of a lower alcohol such as ethanol, isopropanol or butanol.

The aqueous hydrogen peroxide solution may be stabilized, for example, with phenacetin, acetanilide, mono- and trisodium phosphates or with 8-hydroxyquinoline sulphate, and stannates including sodium stannate.

If the tension in the hair was maintained by external means, these means (rollers, curlers and the like) may be removed from the hair before or after the fixing step.

Lastly, in the final step of the process according to the invention (step (iv)), which is also an optional step, the hair impregnated with the oxidizing composition is rinsed thoroughly, generally with water.

The final result is hair which is soft and easy to disentangle. The hair is wavy.

The oxidizing composition according to the invention can also be used in a process for bleaching keratin fibres, and in particular the hair.

The bleaching process according to the invention comprises a step of applying an oxidizing composition according to the invention to the keratin fibres, this composition preferably comprising aqueous hydrogen peroxide solution in an alkaline medium, after extemporaneous mixing. Conventionally, a second step in the bleaching process according to the invention is a step of rinsing the keratin fibres.

Specific examples illustrating the invention will now be given.

Hereinabove and hereinbelow, the percentages are expressed on a weight basis except where otherwise stated.

The examples which follow illustrate the invention without, however, being limiting in nature.

PREPARATION EXAMPLE 2006.2 g of tert-butanol and then 340.0 g of 2-acrylamido-2-methylpropanesulphonic acid are introduced into a 5-litre round-bottomed flask fitted with a stirrer, a reflux condenser, a thermometer and a device for conveying nitrogen and aqueous ammonia, the acid being dispersed in the solution with vigorous stirring. After 30 minutes, aqueous ammonia is added via the upper tube of the flask and the reaction mixture is maintained for 30 minutes at room temperature until a pH of about 6–6.5 is obtained. 19.2 g of 25% trimethylolpropane triacrylate solution in tert-butanol are then added and the reaction medium is heated to 60° C. and is simultaneously made inert by supplying nitrogen into the flask. Once this temperature has been reached, dilauroyl peroxide is added. The reaction starts immediately, as evidenced by an increase in temperature and by precipitation of the polymerizate. 15 minutes after the start of the polymerization, a stream of nitrogen is introduced. 30 minutes after adding the initiator, the temperature of the reaction medium reaches a maximum of 65–70° C. 30 minutes after this temperature has been reached, the mixture is heated to reflux and maintained under these conditions for 2 hours. The formation of a thick paste is observed in the course of the reaction. The mixture is cooled to room temperature and the product obtained is filtered off. The paste recovered is then dried under vacuum at 60–70° C. for 24 hours. 391 g of crosslinked and neutralized poly(2-acrylamido-2-methylpropanesulphonic acid) are obtained, having a viscosity, measured with a Brookfield viscometer, rotor 4, at a spin speed of 100 revolutions/minute in a 2% aqueous solution and at 25° C., of about 7000 cps.

The hydrodynamic radius of the resulting polymer in an aqueous solution, determined by dynamic light scattering, is 160 nm.

Example 1

The inventor carried out a comparative test in order to demonstrate the improvement in shelf life after storage of an oxidizing composition for two months.

Oxidizing composition $A_1$ below, in accordance with the invention, was prepared:

| | |
|---|---|
| Poly(2-acrylamido-2-methylpropanesulphonic acid) crosslinked and neutralized with aqueous ammonia, prepared according to the process of the preparation example, with a viscosity of about 7000 cps in 2% aqueous solution and at 25° C. | 0.27 g |
| 200-volumes hydrogen peroxide | 12 g |
| Stabilizer | qs |
| pH agent | qs pH 4.7 |
| Demineralized water | qs 100 g |

The instantaneous viscosity of composition $A_1$ is about 150 cps.

A comparative oxidizing composition $B_1$, of the same composition as $A_1$ but containing a crosslinked poly(acrylic acid) sold under the name Carbopol 940 by the company Goodrich, in an amount of 0.18% by weight, instead of the crosslinked and neutralized poly(2-acrylamido-2-methylpropanesulphonic acid), in order to obtain a gel having a viscosity of about 150 cps, was also prepared.

A comparative oxidizing composition $C_1$, of the same composition as $A_1$ but containing a crosslinked poly(acrylic acid) sold under the name Carbopol 980 by the company Goodrich, in an amount of 0.17% by weight, instead of the crosslinked and neutralized poly(2-acrylamido-2-methylpropanesulphonic acid), in order to obtain a gel having a viscosity of about 150 cps, was also prepared.

Each of the compositions $A_1$, $B_1$ and $C_1$ is stored for 2 months at 45° C. The relative variation in viscosity during the storage period is then calculated for each composition.

The results of the test are summarized in the following table.

| Formula | Variation in viscosity after storage at 45° C. for 2 months |
|---|---|
| Composition $A_1$ (invention) | +3% |
| Composition $B_1$ (comparative) | −18% |
| Composition $C_1$ (comparative) | −23% |

These results show clearly that the use of a crosslinked poly(2-acrylamido-2-methylpropanesulphonic acid) which is at least 90% by weight neutralized in an oxidizing composition for a permanent reshaping process improves its stability on storage, in contrast with a standard gelling agent of the Carbopol type.

Example 2

OXIDATION DYEING PROCESS

| Dye composition A₂: | |
|---|---|
| Para-phenylenediamine | 0.324 g |
| 1-β-Hydroxyethyloxy-2,4-diaminobenzene dihydrochloride | 0.723 g |
| Oleyl alcohol polyglycerolated with 2 mol of glycerol | 4.0 g |
| Oleyl alcohol polyglycerolated with 4 mol of glycerol, containing 78% active material (A.M.) | 5.69 g A.M. |
| Oleic acid | 3.0 g |
| Oleylamine containing 2 mol of ethylene oxide, sold under the trade name Ethomeen O12 by the company Akzo | 7.0 g |
| Diethylaminopropyl laurylamino succinamate, sodium salt containing 55% A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite as an aqueous solution containing 35% A.M. | 0.455 g A.M. |
| Ammonium acetate | 0.8 g |
| Antioxidant, sequestering agent | qs |
| Fragrance, preserving agent | qs |
| Aqueous ammonia containing 20% NH₃ | 10.0 g |
| Demineralized water | qs 100 g |
| Oxidizing composition B₂: | |
| Poly(2-acrylamido-2-methylpropanesulphonic acid) crosslinked and neutralized with aqueous ammonia, prepared according to the process of the preparation example, with a viscosity of about 7000 cps in 2% aqueous solution and at 25° C. | 0.27 g |
| 200-volumes hydrogen peroxide | 12 g |
| Stabilizer | qs |
| Orthophosphoric acid | qs pH 3.8 |
| Demineralized water | qs 100 g |

Composition A₂ was mixed, at the time of use, with the oxidizing composition B₂.

The mixture obtained was applied for 30 minutes to locks of permanent-waved or non-permanent-waved natural grey hair containing 90% white hairs, in a proportion of 28 g per 3 g.

Intense blue colorations are obtained.

Example 3

PERMANENT RESHAPING PROCESS

A specific example of a reducing composition A₃ and of a fixing (oxidizing) composition B₃ for a process of permanent reshaping of the hair is given below:

| Reducing composition A₃: | |
|---|---|
| Cocoylbetain | 2.0% |
| Thioglycolic acid | 7.0% |
| Ammonium bicarbonate | 5.5% |
| Sequestering agent | 0.4% |
| Aqueous ammonia containing 20% NH₃ | 6.6% |
| Demineralized water | qs 100% |

The reducing composition was prepared by simple mixing.

| Fixing composition B₃: | |
|---|---|
| Poly(2-acrylamido-2-methylpropanesulphonic acid) crosslinked and neutralized with aqueous ammonia, prepared according to the process of the preparation example, with a viscosity of about 7000 cps in 2% aqueous solution and at 25° C. | 0.3 g |
| 200-volumes hydrogen peroxide | 4.8 g |
| Stabilizer | qs |
| Citric acid | qs pH 4 |
| Demineralized water | qs 100 g |

We claim:

1. A cosmetic composition for treating a keratin substance comprising, in a support suitable for a keratin substance:

(a) at least one homopolymer selected from crosslinked and at least 90% neutralized poly(2-acrylamido-2-methylpropanesulphonic acid) homopolymers, and (b) at least one oxidizing agent selected from hydrogen peroxide and compounds capable of producing hydrogen peroxide by hydrolysis.

2. A composition according to claim 1 wherein said at least one polymer comprises, distributed randomly:

a) from 90 to 99.99% by weight, relative to the total weight of the polymer, of units of formula (1) below:

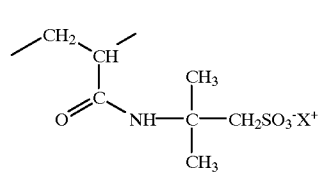

(1)

wherein $X^+$ denotes a cation or a mixture of cations, not more than 10 mol % of which cations $X^+$ may be protons $H^+$;

b) from 0.01 to 10% by weight, relative to the total weight of the polymer, of crosslinking units derived from at least one monomer having at least two olefinic double bonds.

3. A composition according to claim 2 wherein said at least one polymer comprises a number of units of formula (1) in a sufficiently large amount to obtain polymer particles whose hydrodynamic volume in aqueous solution has a radius ranging from 10 to 500 nm and whose distribution is homogeneous and unimodal.

4. A composition according to claim 2 wherein said at least one polymer comprises from 98 to 99.8% by weight of units of formula (1) and from 0.2 to 2% by weight of crosslinking units.

5. A composition according to claim 2 wherein said cation $X^+$ is $NH_4^+$.

6. A composition according to claim 1 wherein said at least one polymer comprises crosslinking units derived from at least one monomer of formula (2) below:

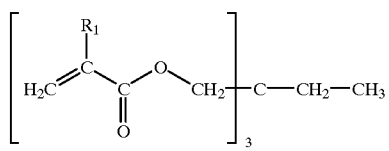

(2)

wherein $R_1$ denotes hydrogen or a $C_1$–$C_4$ alkyl.

7. A composition according to claim 1 wherein said at least one polymer is crosslinked with trimethylolpropane triacrylate.

8. A composition according to claim 1 wherein said at least one polymer has a viscosity of at least 1000 cps.

9. A composition according to claim 8, wherein said viscosity is measured with a Brookfield viscometer in an aqueous 2% solution and at 25° C.

10. A composition according to claim 8 wherein said viscosity ranges from 5000 to 40,000 cps.

11. A composition according to claim 10, wherein said viscosity is measured with a Brookfield viscometer in an aqueous 2% solution and at 25° C.

12. A composition according to claim 10 wherein said viscosity ranges from 6500 to 35,000 cps.

13. A composition according to claim 12, wherein said viscosity is measured with a Brookfield viscometer in an aqueous 2% solution and at 25° C.

14. A composition according to claim 1 wherein said at least one polymer is present in concentrations ranging from 0.01 to 10% by weight relative to the total weight of the composition.

15. A composition according to claim 1 wherein said concentrations range from 0.05 to 5% by weight relative to the total weight of the composition.

16. A composition according to claim 1 wherein said at least one oxidizing agent is selected from hydrogen peroxide, urea peroxide, perborates and persulphates.

17. A composition according to claim 1 wherein said at least one oxidizing agent is hydrogen peroxide.

18. A composition according to claim 17 wherein the hydrogen peroxide concentration ranges from 0.5 to 40 volumes.

19. A composition according to claim 18 wherein said hydrogen peroxide concentration ranges from 2 to 30 volumes.

20. A composition according to claim 1 wherein the concentration of said at least one compound capable of producing hydrogen peroxide by hydrolysis ranges from 0.1 to 25% by weight relative to the total weight of the composition.

21. A composition according to claim 1 wherein said composition is aqueous and has a pH ranging from 1 to 12.

22. A composition according to claim 21 wherein said pH ranges from 2 to 12.

23. A composition according to claim 1 wherein said composition is in the form of a transparent gel with a viscosity ranging from 50 centipoises to 100 poises.

24. A composition according to claim 23 wherein said viscosity ranges from 75 centipoises to 5 poises.

25. A process for the oxidation dyeing of keratin fibres comprising the step of applying to said fibres
a dye composition comprising, in a support which is suitable for dyeing keratin fibres, at least one oxidation dye precursor and
a composition according to claim 1.

26. A process according to claim 25 wherein said keratin fibres are human keratin fibres.

27. A process according to claim 26 wherein said human keratin fibres are hair.

28. A process according to claim 25 wherein said dye composition comprising, in a support which is suitable for dyeing keratin fibres, at least one oxidation dye precursor is mixed, at the time of use, with said composition comprising (a) at least one polymer selected from crosslinked and at least 90% neutralized poly(2-acrylamido-2-methylpropanesulphonic acid) polymers, and (b) at least one oxidizing agent selected from hydrogen peroxide and compounds capable of producing hydrogen peroxide by hydrolysis, and thereafter said dye composition and said composition comprising (a) and (b) are applied to the keratin fibres and left in place for 3 to 50 minutes after which the fibres are rinsed, washed with shampoo, rinsed again and dried.

29. A process according to claim 28 wherein said dye composition and said composition comprising (a) and (b) are left in place for 5 to 30 minutes.

30. A process according to claim 25 wherein said composition comprising (a) and (b) is applied to said fibres and thereafter said dye composition is applied to said fibres with or without intermediate rinsing.

31. A process according to claim 25 wherein said dye composition is applied to said fibres and thereafter said composition comprising (a) and (b) is applied to said fibres with or without intermediate rinsing.

32. A process for obtaining permanent reshaping of a keratin substance comprising the steps of: (i) applying a reducing composition to the keratin substance to be treated, said keratin substance being placed under mechanical tension before, during or after the said application, (ii) optionally rinsing the keratin substance, (iii) applying a composition according to claim 1 to the optionally rinsed keratin substance, and (iv) optionally rinsing the keratin substance again.

33. A process according to claim 32 wherein said keratin substance is hair.

34. A process according to claim 33 wherein said hair is permanently reshaped in the shape of permanent-waved hair.

35. A process for bleaching a keratin substance comprising the steps of: i) applying to the keratin substance a composition according to claim 1, and (ii) rinsing the keratin substance thus treated.

36. A process according to claim 35 wherein said keratin substance is hair.

37. A process comprising the step of including at least one polymer according to claim 1 in an amount effective as a thickener and/or gelling agent in a cosmetic or dermatological composition comprising at least one oxidizing agent selected from hydrogen peroxide and compounds capable of producing hydrogen peroxide by hydrolysis.

* * * * *

UNITED STATES PATENT AND TRADEMARK OFFICE
CERTIFICATE OF CORRECTION

PATENT NO. : 6,180,118 B1
DATED : January 30, 2001
INVENTOR(S) : Mireille Maubru et al.

It is certified that error appears in the above-identified patent and that said Letters Patent is hereby corrected as shown below:

Claim 15, Column 11,
Line 34, "claim 1" should read --claim 14--.

Claim 21, Column 11,
Line 54, "1 to 12" should read --1 to 13--.

Claim 28, Column 12,
Line 21, after "50 minutes" insert --,--.

Signed and Sealed this

Seventeenth Day of July, 2001

*Attest:*

NICHOLAS P. GODICI
*Attesting Officer*    Acting Director of the United States Patent and Trademark Office